(12) United States Patent
Akiyama et al.

(10) Patent No.: US 8,872,907 B2
(45) Date of Patent: Oct. 28, 2014

(54) ENDOSCOPE APPARATUS

(71) Applicant: Olympus Medical Systems Corp., Tokyo (JP)

(72) Inventors: Daisuke Akiyama, Tokyo (JP); Tsutomu Uzawa, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/966,343

(22) Filed: Aug. 14, 2013

(65) Prior Publication Data

US 2014/0055585 A1 Feb. 27, 2014

Related U.S. Application Data

(63) Continuation of application No. PCT/JP2013/050841, filed on Jan. 17, 2013.

(30) Foreign Application Priority Data

Feb. 21, 2012 (JP) ................. 2012-035201

(51) Int. Cl.
*A61B 1/06* (2006.01)
*G02B 23/24* (2006.01)
*G02B 23/26* (2006.01)
*A61B 1/00* (2006.01)

(52) U.S. Cl.
CPC .......... *A61B 1/0676* (2013.01); *G02B 23/2469* (2013.01); *A61B 1/00009* (2013.01); *A61B 1/0638* (2013.01); *G02B 23/26* (2013.01); *G02B 23/2423* (2013.01); *A61B 1/00172* (2013.01)
USPC ......................................................... 348/68

(58) Field of Classification Search
CPC ........... G02B 23/2423; G02B 23/2469; G02B 23/26; A61B 1/0638; A61B 1/0676; A61B 1/00009; A61B 1/00172
USPC ......................................................... 348/68
See application file for complete search history.

(56) References Cited

U.S. PATENT DOCUMENTS 6,294,775 B1    9/2001   Seibel et al.
2010/0123775 A1 5/2010   Shibasaki

FOREIGN PATENT DOCUMENTS

| JP | 07-124100 A | 5/1995 |
| JP | 07-275192 A | 10/1995 |
| JP | 10-161041 A | 6/1998 |
| JP | 2010-115391 A | 5/2010 |
| JP | 2010-268961 A | 12/2010 |
| JP | 2011-101665 A | 5/2011 |

OTHER PUBLICATIONS

International Search Report dated Apr. 2, 2013 received in related International Application No. PCT/JP2013/050841.

*Primary Examiner* — Andy Rao
*Assistant Examiner* — Nguyen Truong
(74) *Attorney, Agent, or Firm* — Scully, Scott, Murphy & Presser, P.C.

(57) ABSTRACT

Provided is an endoscope apparatus including a light-guiding part that guides illumination light emitted from a light source to the distal end of an inserted portion; a scanning part that makes the light-guiding part vibrate with a predetermined period, thus two-dimensionally scanning the illumination light emitted from the inserted portion on an observation subject; an image-acquisition part that receives return light of the illumination light coming from the observation subject and that generates an image signal based on a position scanned by the scanning part and an intensity of the return light; and a light-source control part that controls the light source so as to change the intensity of the illumination light emitted from the inserted portion in accordance with an angle formed between the longitudinal direction of the inserted portion and a direction in which the illumination light is emitted toward the observation subject.

4 Claims, 3 Drawing Sheets

ENDOSCOPE APPARATUS

CROSS-REFERENCE TO RELATED APPLICATIONS

This is a continuation of International Application PCT/JP2013/050841, with an international filing date of Jan. 17, 2013, which is hereby incorporated by reference herein in its entirety.
This application is based on Japanese Patent Application No. 2012-035201, filed on Feb. 21, 2012, the contents of which are incorporated herein by reference.

TECHNICAL FIELD

The present invention relates to an endoscope apparatus, and, in particular, to an endoscope apparatus with which the level of illumination light radiated onto an observation subject can be adjusted.

BACKGROUND ART

In a so-called scanning endoscope apparatus, the distal end of a light-guide fiber provided in an inserted portion is vibrated by an actuator or the like, and, by doing so, illumination light guided from a light source is emitted from the light-guide fiber and is scanned on an observation subject. Then, desired observation is performed by acquiring an image of the observation subject based on the scanning position on the observation subject and the intensity of light that is reflected at the scanning position.

In such an endoscope apparatus, when the intensity of illumination light radiated onto the observation subject is always constant in a frame that forms one image, a dark portion, halation, and so forth tend to occur in the acquired image. In particular, when the observation subject is a luminal structure such as a digestive tract or the like, the center of the image becomes extremely dark whereas a peripheral portion becomes excessively bright, which tends to cause halation.

Because of this, Patent Literature 1 discloses an endoscope apparatus that adjusts the illumination light level in an arbitrary area in accordance with the scanning position of the illumination light based on the brightness/darkness information of an acquired frame image.

CITATION LIST

Patent Literature

{PTL 1} Japanese Unexamined Patent Application, Publication No. 2010-115391

SUMMARY OF INVENTION

The present invention provides an endoscope apparatus with which local brightness/darkness and halation in an observation image can be suppressed, thus making it possible to perform satisfactory observation by accurately depicting even local shading of an observation subject.

The present invention provides the following solutions.
An aspect of the present invention is an endoscope apparatus provided with a light-guiding part that guides illumination light emitted from a light source to the distal end of an inserted portion; a scanning part that makes the light-guiding part vibrate with a predetermined period, thus two-dimensionally scanning the illumination light emitted from the inserted portion on an observation subject; an image-acquisition part that receives return light of the illumination light coming from the observation subject and that generates an image signal based on a position scanned by the scanning part and an intensity of the return light; and a light-source control part that controls the light source so as to change the intensity of the illumination light emitted from the inserted portion in accordance with an angle formed between the longitudinal direction of the inserted portion and a direction in which the illumination light is emitted toward the observation subject.

In the above-described aspect of the endoscope apparatus according to the present invention, it is preferable that the light-source control part control the light source so that an intensity $I1(\theta)$ of the illumination light emitted from the light source satisfies Expressions (1) and (2) below:

{Eq. 1}

$$I_1(\theta) = A f(\theta) \tag{1}$$

$$1 - \sin^{2.5}\theta \le f(\theta) \le 1 - \sin^7 \theta \tag{2}$$

Here, $\theta$ is an angle formed between the longitudinal direction of the inserted portion and the emitting direction of the illumination light emitted from the inserted portion, and A is the intensity of illumination light emitted from the inserted portion when $\theta = 0$.

By doing so, brightness/darkness differences and halation can be suppressed in an acquired observation image.

It is preferable that the above-described aspect of the endoscope apparatus according to the present invention be provided with an optical member that is disposed at the light-guiding part on the distal-end side of the inserted portion and that is treated with an anti-reflection treatment or an optical member that increases an observation angle, wherein the light-source control part controls the light source so that the intensity of the illumination light emitted from the light source to the light-guiding part is increased with an increase in the angle.

In the above-described aspect of the endoscope apparatus according to the present invention, it is preferable that the light-source control part control the light source so that an intensity $I2(\theta)$ of the illumination light emitted from the light source satisfies Expressions (3) and (4) below:

{Eq. 2}

$$I_2(\theta) = A f(\theta) \tag{3}$$

$$\frac{1}{\cos\theta} \le f(\theta) \le \frac{1}{\cos^5\theta} \tag{4}$$

Here, $\theta$ is an angle formed between the longitudinal direction of the inserted portion and the emitting direction of the illumination light emitted from the inserted portion, and A is the intensity of illumination light emitted from the inserted portion when $\theta = 0$.

DESCRIPTION OF EMBODIMENT

An endoscope apparatus according to an embodiment of the present invention will be described below with reference to the drawings.

Figure 1:
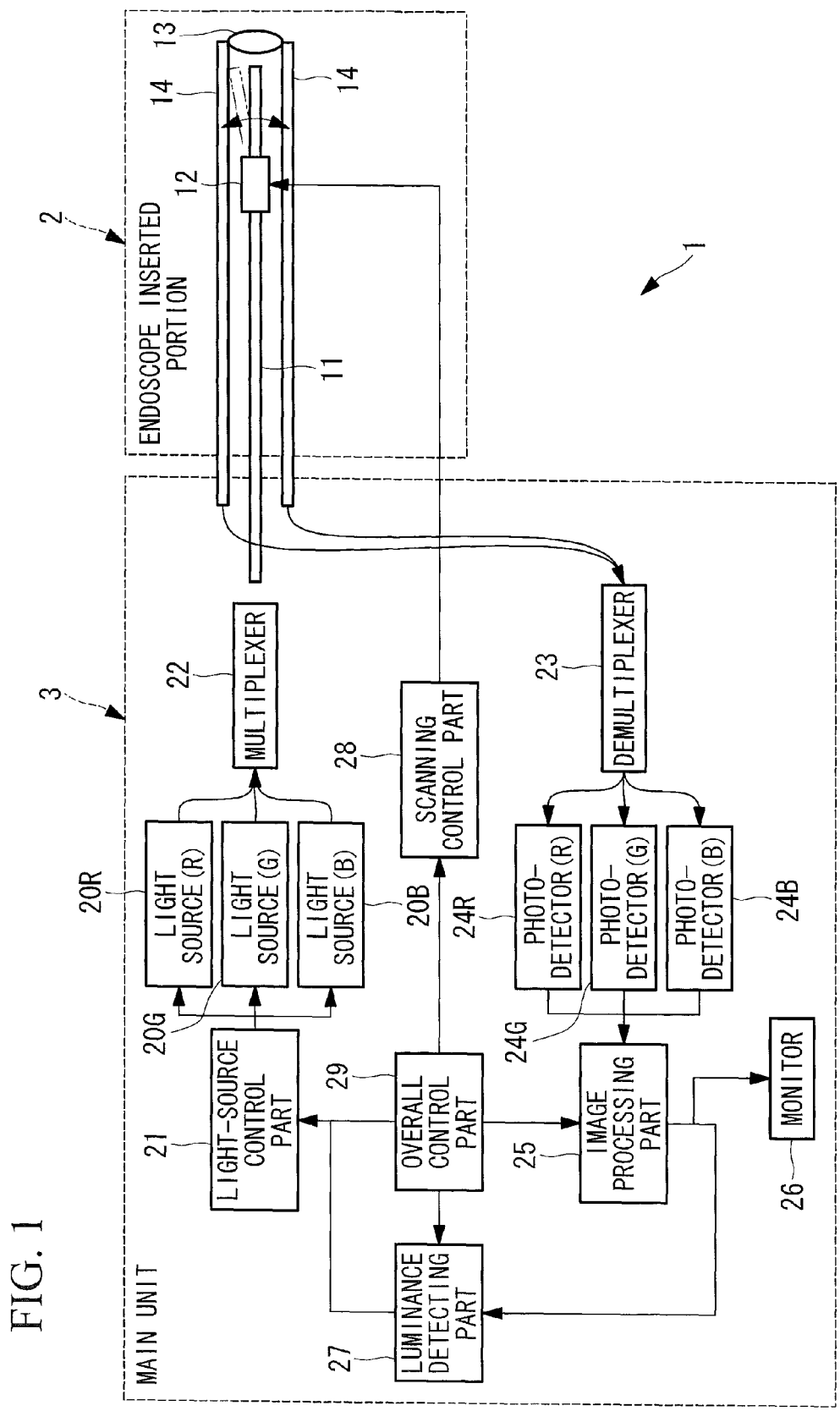
FIG. 1 is a diagram showing, in outline, the configuration of an endoscope apparatus according to an embodiment of the present invention.

FIG. 1 is a diagram showing, in outline, the configuration of an endoscope apparatus according to this embodiment; as shown in FIG. 1, an endoscope apparatus 1 is provided with an inserted portion 2 and a main unit 3. The inserted portion 2 is provided with a light-guide fiber (light-guiding part) 11, an actuator (scanning part) 12, a lens 13, and a light-receiving fiber 14.

The main unit 3 is provided with light sources 20R, 20G, and 20B, a light-source control part 21, a multiplexer 22, a demultiplexer 23, photodetectors 24R, 24G, and 24B, an image processing part 25 (image-acquisition part), a monitor 26, a luminance detecting part 27, a scanning control part 28, and an overall control part 29.

The light-guide fiber 11 guides illumination light emitted from the light sources, described later, to the distal end of the inserted portion, and the lens 13, which is provided at the light-guide fiber 11 on the distal-end side of the inserted portion, spreads out the illumination light from the light-guide fiber 11 and emits the illumination light toward an observation subject. The actuator 12 makes the light-guide fiber 11 vibrate with a predetermined period, thus two-dimensionally scanning the illumination light emitted from the inserted portion on the observation subject. As the actuator 12, for example, a piezoelectric device can be employed, and the orientation of the distal end of the light-guide fiber 11 is changed by making the distal end of the light-guide fiber 11 oscillate in two perpendicular directions in accordance with instructions from the scanning control part 28, described later, which causes the illumination light to follow a helical scanning trajectory on the observation subject. The light-receiving fiber 14 receives return light of the illumination light coming from the observation subject.

Figure 2:
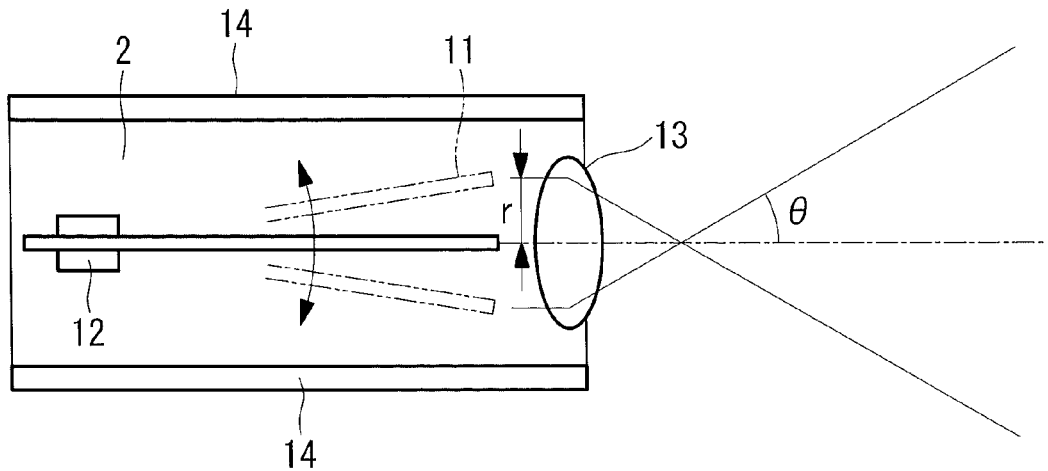
FIG. 2 is a diagram showing, in outline, the configuration of an inserted portion of the endoscope apparatus according to the embodiment of the present invention.

The light sources 20R, 20G, and 20B emit R, G, and B beams, respectively, and are driven and controlled by means of the light-source control part 21. In addition to driving and controlling the light sources 20R, 20G, and 20B, the light-source control part 21 controls the light sources 20R, 20G, and 20B so as to change the intensity of the illumination light emitted from the inserted portion in accordance with an angle θ formed between the longitudinal direction of the inserted portion and the direction in which the illumination light is emitted toward the observation subject (see FIG. 2).

In particular, the light-source control part 21 controls the light sources 20R, 20G, and 20B so that the intensity of the illumination light emitted from the inserted portion decreases with an increase in the angle θ. More specifically, the light sources 20R, 20G, and 20B are controlled so that an intensity I(θ) of the illumination light emitted from the light sources satisfies Expressions (5) and (6) below.

{Eq. 3}

$$I(\theta) = A f(\theta) \tag{5}$$

$$1 - \sin^{2.5}\theta \leq f(\theta) \leq 1 - \sin^{7}\theta \tag{6}$$

In addition, it is more preferable that the light sources 20R, 20G, and 20B be controlled so as to satisfy Expression (7) below.

{Eq. 4}

$$I(\theta) = A(1 - \sin^{\alpha}(\beta\theta)) \tag{7}$$

Figure 3:
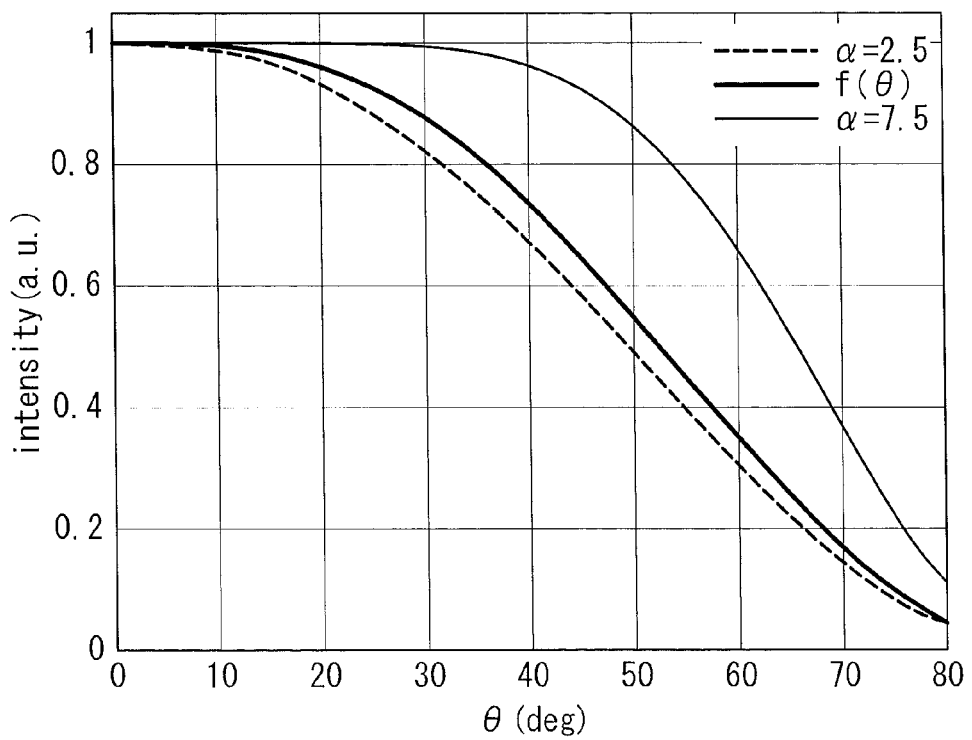
FIG. 3 is a graph showing the relationship between the intensity $I(\theta)$ of illumination light and an angle $\theta$ formed with respect to the emitting direction of the illumination light emitted from the inserted portion.

Here, θ is an angle formed between the longitudinal direction of the inserted portion and the emitting direction of the illumination light emitted from the inserted portion, and A is the intensity of illumination light emitted from the inserted portion when θ=0; and θ and A can be determined based on the luminance information of previously acquired image signals.

α is a coefficient that indicates the relative shape of a light distribution, and it is preferable that α be determined in accordance with the type of observation subject. For example, it is preferable that α=2.5 when the observation subject is a lumen such as a pancreatic duct, and that α=4 to 5 when the observation subject is a large space such as stomach or the like, or flat as in the case of close-range observation or the like. It is also possible to change the value of α in accordance with the magnitude of A. β is a coefficient depending on the viewing angle of the endoscope apparatus, and, because the light-level ratio of the center and peripheral portions in an acquired observation image differs depending on the viewing angle, β is determined in consideration of this fact. Assuming the maximum angle of the viewing angle to be Θ, it is preferable that β be such that β=Θ/70. The relationship between the intensity I(θ) of the illumination light and the angle θ is shown in FIG. 3.

Figure 4:
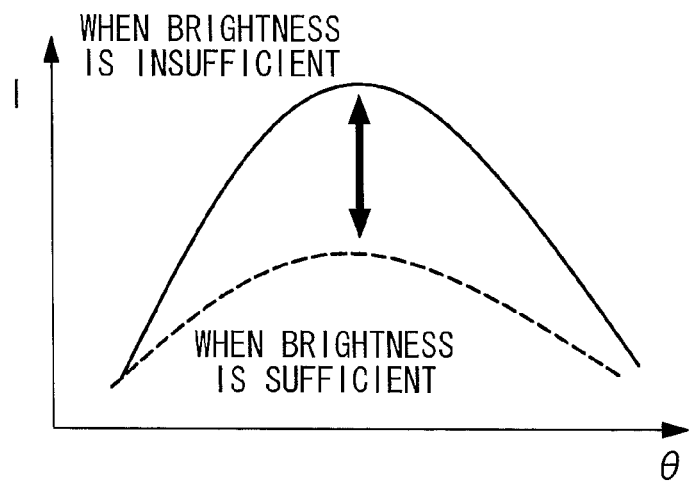
FIG. 4 is a graph showing an overall brightness balance in an observation image for the endoscope apparatus according to the embodiment of the present invention.

In addition, the light-source control part 21 controls the light sources 20R, 20G, and 20B based on the luminance information of an image signal acquired by the luminance detecting part 27, described later. Specifically, for example, in the case in which the entire observation image is dark or bright due to the environment in which the image is acquired and the characteristics of the light-receiving fiber 14 and the image processing part 25, as shown in the graph shown in FIG. 4, it is possible to acquire a satisfactory observation image by adjusting the brightness of the entire observation image without altering the relative changes in the intensity of the illumination light in an acquired observation image, in other words, by adjusting the absolute brightness of the entire image while maintaining the changes in the intensity of the illumination light among angles θ. This can be achieved by changing the value of A described above, and the value can be determined based on an average value of the luminance information for a plurality of frames, in addition to the luminance information for 1 frame acquired by the luminance detecting part 27.

The multiplexer 22 multiplexes beams emitted from the light sources 20R, 20G, and 20B, and supplies the light-guide fiber 11 with illumination light in the form of white light. The demultiplexer 23 demultiplexes the return light from the observation subject, which enters thereinto via the light-receiving fiber 14, into R, G, and B beams, and transmits the respective demultiplexed R, G, and B beams to the photodetectors 24R, 24G, and 24B. The photodetectors 24R, 24G, and 24B generate pixel signals in accordance with the intensities of the respective R, G, and B beams from the demultiplexer 23, and output the generated individual pixel signals to the image processing part 25. The image processing part 25 generates an image signal for 1 frame based on the pixel signals from the photodetectors 24R, 24G, and 24B and the scanning position of the illumination light. The monitor 26 displays an image of the observation subject based on the generated image signal.

The luminance detecting part 27 detects the luminance information, which is the intensity of the return light, based on the image signal generated at the image processing part 25. The scanning control part 28 outputs predetermined instruction signals to the actuator 12 in order to make the light-guide fiber 11 vibrate with the predetermined period, thereby driving and controlling the actuator 12. The overall control part 29 includes a CPU, a ROM, and a RAM (not shown) and controls the operation of the main unit 3 in accordance with a program stored in the ROM for operating and controlling the endoscope apparatus 1.

When acquiring an observation image by using the thus-configured endoscope apparatus, the light sources 20R, 20G, and 20B emit R, G, and B beams, respectively, based on the instructions from the light-source control part 21, and the emitted respective beams are multiplexed at the multiplexer 22 to form the white illumination light, which is supplied to the light-guide fiber 11. The supplied illumination light is helically scanned on the observation subject by the light-guide fiber 11. At this time, the beams emitted from the light sources 20R, 20G, and 20B have intensities in accordance with the angle θ, with respect to the longitudinal direction of the inserted portion, of the illumination light that is emitted from the light-guide fiber 11 and that is emitted from the inserted portion via the lens 13. Because of this, the illumination light is evenly distributed over the observation subject regardless of the position in the observation subject.

The return light reflected at the observation subject is transmitted to the demultiplexer 23 via the light-receiving fiber 14 and is demultiplexed at the demultiplexer 23 into individual R, G, and B beams, which are converted into pixel signals at the photodetectors 24R, 24G, and 24B in accordance with the intensities of the respective beams. The converted pixel signals are output to the image processing part 25, and an image signal for 1 frame is generated at the image processing part 25 based on the pixel signals and the scanning position of the illumination light.

By doing so, during a unit scanning period for acquiring an image signal for 1 frame, the emitting angle of the illumination light emitted from the inserted portion is decreased; the intensity of the illumination light is relatively increased in an image that forms the center of an observation image; the intensity of the illumination light is relatively decreased at a peripheral portion of the distal end of the inserted portion, where the emitting angle of the illumination light emitted from the inserted portion is large; and thus, local brightness/darkness differences and halation can be suppressed in an acquired observation.

(Modification)

In the embodiment described above, the lens 13 does not require special optical characteristics, and, for example, a cover glass or the like can be employed. However, for example, a lens in which the lens 13 is treated with an AR coating treatment, a wide-angle lens, or the like is employed in some cases, and, in such a case, the light-source control part 21 needs to control the light sources 20R, 20G, and 20B as described below.

Specifically, in the case in which a lens that is treated with an AR coating (anti-reflection) treatment or a wide-angle lens that increases the observation angle is disposed at the light-guide fiber 11 on the distal-end side of the inserted portion, these lenses increase a loss in the light distribution at a peripheral portion of the distal end of the inserted portion, thus decreasing the light level of the illumination light distributed to the peripheral portion.

Therefore, in such a case, the light sources are controlled so that the intensity of the illumination light to be supplied to the light-guide fiber 11 from the light sources 20R, 20G, and 20B increases with an increase in the emitting angle θ of the illumination light emitted from the inserted portion.

Specifically, it is preferable that the light-source control part 21 control the light sources so that the intensity I(θ) of the illumination light emitted from the light sources 20R, 20G, and 20B satisfies Expressions (8) and (9) below.

{Eq. 5}

$$I(\theta) = Af(\theta) \tag{8}$$

$$\frac{1}{\cos\theta} \leq f(\theta) \leq \frac{1}{\cos^5\theta} \tag{9}$$

Figure 5:
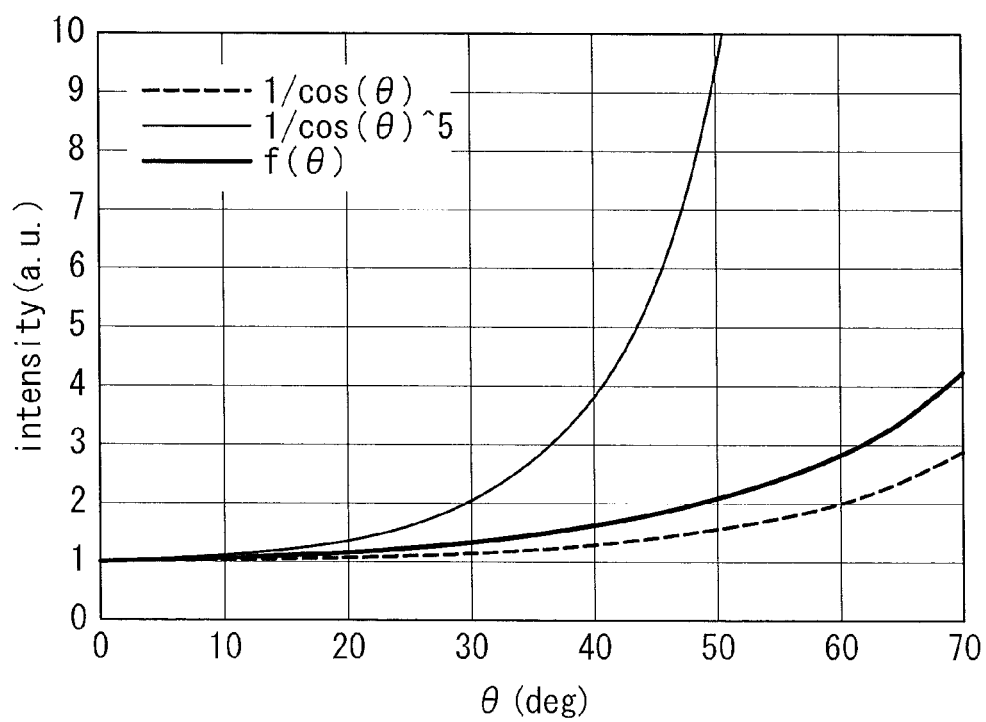
FIG. 5 is a graph showing the relationship between the intensity I(θ) of illumination light and the angle θ formed with respect to the emitting direction of the illumination light emitted from the inserted portion.

Here, θ is an angle formed between the longitudinal direction of the inserted portion and the emitting direction of the illumination light emitted from the inserted portion, and A is the intensity of illumination light emitted from the inserted portion when θ=0. The relationship between an intensity I1(θ) of the illumination light and the angle θ is shown in FIG. 5.

By doing so, these lenses consequently decrease the emitting angle of the illumination light emitted from the inserted portion, relatively increase the intensity of the illumination light in an image forming the center of an observation image, relatively decrease the intensity of the illumination light at a peripheral portion of the distal end of the inserted portion, where the emitting angle of the illumination light emitted from the inserted portion is large, and thus, local brightness/darkness differences and halation can be suppressed in an acquired observation image.

REFERENCE SIGNS LIST 1 endoscope apparatus
2 inserted portion
11 light-guide fiber
12 actuator
13 lens
14 light-receiving fiber
20R, 20G, 20B light source R, light source G, light source B
21 light-source control part
22 multiplexer
23 demultiplexer
24R, 24G, 24B photodetector R, photodetector G, photodetector B
25 image processing part
26 monitor
27 luminance detecting part
28 scanning control part
29 overall control part

The invention claimed is:
1. An endoscope apparatus comprising:
a light-guiding part that guides illumination light emitted from a light source to the distal end of an inserted portion;

a scanning part that makes the light-guiding part vibrate with a predetermined period, thus two-dimensionally scanning the illumination light emitted from the inserted portion on an observation subject;

an image-acquisition part that receives return light of the illumination light coming from the observation subject and that generates an image signal based on a position scanned by the scanning part and an intensity of the return light; and a light-source control part that controls the light source so as to change the intensity of the illumination light emitted from the inserted portion in accordance with an angle formed between the longitudinal direction of the inserted portion and a direction in which the illumination light is emitted toward the observation subject, wherein the light-source control part controls the light source so that an intensity $I1(\theta)$ of the illumination light emitted from the light source satisfies Expressions (1) and (2) below:

{Eq. 1}

$$I_1(\theta) = Af(\theta) \tag{1}$$

$$1-\sin^{2.5}\theta \leq f(\theta) \leq 1-\sin^7\theta \tag{2}$$

where $\theta$ is an angle formed between the longitudinal direction of the inserted portion and the emitting direction of the illumination light emitted from the inserted portion, and A is the intensity of illumination light emitted from the inserted portion when $\theta=0$.

2. An endoscope apparatus comprising:

a light-guiding part that guides illumination light emitted from a light source to the distal end of an inserted portion;

a scanning part that makes the light-guiding part vibrate with a predetermined period, thus two-dimensionally scanning the illumination light emitted from the inserted portion on an observation subject;

an image-acquisition part that receives return light of the illumination light coming from the observation subject and that generates an image signal based on a position scanned by the scanning part and an intensity of the return light;

a light-source control part that controls the light source so as to change the intensity of the illumination light emitted from the inserted portion in accordance with an angle formed between the longitudinal direction of the inserted portion and a direction in which the illumination light is emitted toward the observation subject; and an optical member that is disposed at the light-guiding part on the distal-end side of the inserted portion and that is treated with an anti-reflection treatment or an optical member that increases an observation angle, wherein the light-source control part controls the light source so that the intensity of the illumination light emitted from the light source to the light-guiding part is increased with an increase in the angle, and also controls the light source so that an intensity $I2(\theta)$ of the illumination light emitted from the light source satisfies Expressions (3) and (4) below:

{Eq. 2}

$$I_2(\theta) = Af(\theta) \tag{3}$$

$$\frac{1}{\cos\theta} \leq f(\theta) \leq \frac{1}{\cos^5\theta} \tag{4}$$

where $\theta$ is an angle formed between the longitudinal direction of the inserted portion and the emitting direction of the illumination light emitted from the inserted portion, and A is the intensity of illumination light emitted from the inserted portion when $\theta=0$.

3. An endoscope apparatus according to claim 1, further comprising:

a luminance detecting part that detects luminance information, which is the intensity of the return light, based on the image signal, wherein the light-source control part controls the light source based on the luminance information from the luminance detecting part.

4. An endoscope apparatus according to claim 2, further comprising:

a luminance detecting part that detects luminance information, which is the intensity of the return light, based on the image signal, wherein the light-source control part controls the light source based on the luminance information from the luminance detecting part.

* * * * *